United States Patent [19]

Benfer, Jr.

[11] 4,345,404

[45] Aug. 24, 1982

[54] TREE SURGERY METHODS

[76] Inventor: Neil A. Benfer, Jr., Rte. 3, Box 313, Tappahannock, Va. 22560

[21] Appl. No.: 181,248

[22] Filed: Sep. 3, 1980

[51] Int. Cl.³ ............................................. A01N 3/04
[52] U.S. Cl. ................................................ 47/8; 47/58
[58] Field of Search ........................................ 47/8, 58

[56] References Cited

U.S. PATENT DOCUMENTS

| 1,255,089 | 1/1918 | Freeman | 47/8 |
|---|---|---|---|
| 1,799,699 | 4/1931 | Peets | 47/8 |
| 1,799,700 | 4/1931 | Peets | 47/8 |
| 2,147,866 | 2/1939 | Van Yahres | 47/8 |
| 3,286,400 | 11/1966 | Gruenewaelder | 47/8 |

FOREIGN PATENT DOCUMENTS

| 2247771 | 4/1974 | Fed. Rep. of Germany | 47/8 |
|---|---|---|---|
| 54-40145 | 3/1979 | Japan | 47/8 |

OTHER PUBLICATIONS

J. C. Whitney & Co. Catalog for 1981, #416C, p. 118.

Primary Examiner—Robert E. Bagwill
Attorney, Agent, or Firm—Robert L. Spicer, Jr.

[57] ABSTRACT

This invention relates to the art of certain new and useful improvements in means and methods for shrub and tree surgery, and more particularly to a use of fiberglass and fiberglass resin and hardener techniques to more effectively treat tree wounds and cavities. Such methods and means have been found more successful than other tree surgery methods now in use, i.e., the use of concrete filler, sheet metal plates, etc. for permanent tree healing and for insect and element protection.

Two procedures are used, dictated by the type of injury, (1) a combination of fiberglass resin and hardener can be applied directly to damaged exposed wood tissue (where branches up to 12 inches in diameter have just been removed, or other exposed tissue areas such as trunks, roots, pruned limb ends, etc.) to serve as an effective sealant and to provide a substrata or base on which new cambium growth can readily attach, and (2) where there are large wounds or cavities a combination of properly placed fiberglass cloth, fiberglass resin, and hardener can be used to seal and/or bridge a cavity. These procedures promote new cambium growth, provides protection until the new growth provides permanent protection, strengthens the tree, prevents insect and elements egress and extends tree life.

6 Claims, No Drawings

TREE SURGERY METHODS

OBJECTS OF THE INVENTION

The primary objects of the present invention are to provide advantages of the above referred to fiberglass techniques over other practices: the mixture of resin and hardener bonds well to wood to form both a moisture-proof and airproof seal and a base on which new cambium growth will attach; the fiberglass cover and mixture applied thereto provides a bond and seal that is effective longer than other sealants presently used on tree wounds; the material is light and compact and easy to handle when working in the top of tall trees which provides an added degree of safety at high heights,—a feature that makes treatment of extensive wounds, such as lightning strikes, possible; subsequent patching of adjacent areas is possible, thereby creating a continuous treated area through separate applications; the hardened material will not damage the cutting chain of a chainsaw; there are no bulky or heavy tools or apparatus required; material cost is reduced over known method now in use as is the time required to dress a wound or cavity and the appearance of the treated tree is improved. Further, the materials may also be used to close cavities other than for shrubs or trees.

THE INVENTION

Tree decay begins when natural or manmade wounds (breaks in the protective bark) expose the cambial tissue (xylem and phloem) or heartwood to organisms (insects, bacteria, fungi) associated with the decay process. These organisms, separately or in combination, infect the wood and cause its decay. The tree reacts to wounds by forming a new protective wall (by simultaneous growth of cambial tissue and bark, sometimes called "callus tissue"). The success of this natural process depends on how fast the new protective layer can close the wound in advance of decay, which it cannot do when wounds are large or where large cavities were allowed to develop.

The fiberglass technique is the only method to completely eliminate the moisture and air required by decay-causing organisms to live and multiply. Fiberglass resin and hardener can be applied on new surface wounds directly, and where branches up to 12 inches in diameter have just been removed, to form a longer-lasting seal than other substances. This permits cambium growth to bridge the scar and form a natural protective layer before any decay-causing organisms can break the seal. Where there are large wounds, and cavities already in existance, fiberglass cloth, fiberglass resin, and hardener are used to therover to make a moisture-proof and air-proof seal and to provide further a surface onto which new cambium growth will readily bond and bridge the gap thereby closing the cavity. Traditional procedures for preserving trees that have large wounds or cavities are concrete filler and sheet metal plates. Neither seals tightly, and neither bonds well with wood. Concrete leaves moisture and, when it cures, it contracts to prevent a tight seal which is required. Sheet metal does not form a tight seal and is difficult to handle. The combination of fiberglass cloth, fiberglass resin, and hardener provides the only effective long-term protection, strengthens the structural characteristics of the tree, and can extend the life of the tree for many years. This technique and method can be used for subsequent patching and to treat adjacent wounds, forming a continuous treated area. This is difficult to do effectively using other methods.

The fiberglass technique or method prevents and eliminates tree decay by water-proofing and air-proofing wounds and cavities and provides for and enhances new cambium (callus tissue) growth across repaired injured treated areas and cavities. The procedure for treating surface wounds require that the bark and dead or injured cambium be removed from around the wound, using a sharp cutting tool to do so, and to shape the wound or area of repair in the form of an ellipse or oval when possible and to further cut or taper (scribe) the edge of the wound from outside to inside across the interface of bark and cambium. In doing this, the outer edge of the wound or area to be repaired will have a (slightly) greater diameter than the inner edge of the wound. It is important that the cambium be healthy and that it is firmly adhered to the heartwood. In deeper wounds, a piece of fiberglass cloth is cut to the shape of the wound and is stapled ¼ to ½ inch inside the cambium area exposed by scribing. This covers and bridges the area and thereby closes the wound. If desired, prior to sealing the cavity, the wound may be treated with Benlate and Chlordane to eliminate existing disease organisms and/or insects. The fiberglass resin and hardener are mixed and applied to the entire wound area, thereby coating the exposed heartwood and cambium; and, in the deeper wounds, the attached fiberglass cloth over the opening is also coated. By applying the coating over the exposed cambium new cambium growth will break through the fiberglass sealant and form a new protective wall. After the coating is allowed to harden an additional fiberglass resin and hardener may be applied as necessary to form a tight seal and to further obtain a complete bond between the cloth and tree wood and to also assure a complete covering of the cloth surface.

Where a cavity exists and callus tissue has begun to grow and roll inside the edge of the cavity, the callus tissue is cut or severed at a bevel to clearly expose the cambium layer around the entire circumference of the cavity. The cut should taper at approximately a 45-degree bevel from outside to inside so that the outside diameter of the cavity is slightly larger than the inside diameter of the exposed cambium layer. The tapered cut should extend far enough outward to insure that all the cambium tissue is healthy (not discolored or diseased). The cavity is fumigated with Benlate and Chloradane to eliminate existing disease organisms and/or insects before applying fiberglass cloth. A piece of fiberglass cloth is used to bridge the cavity, cut to the shape of the cavity and tacked or stapled along its edge ¼ to ½ inch inside the exposed cambium layer. The fiberglass resin and hardener are mixed and applied to both the entire exposed cambium layer and cloth surface. The coating is then allowed to harden and additional fiberglass resin and hardener are applied as necessary to form a tight seal. This coating provides for a complete bond between the cloth and treated edge of the cavity, and to completely cover the surface of the cloth which is impregnable to insects and elements. If the cavity is to be filled, an expanding self-hardening foam such as polystyrene, polyurethane, vinyl chloride, etc., may be used. Also, either the resin or hardener may be stained to provide a coloring, consistent with that of the natural color of the tree treated.

It is pointed out that the repair to cavities and recesses, other than trees, are equally appliable to this invention and various modifications are apparent and would not depart from the nature and scope of this invention.

I claim:

1. The method of repairing a wound on a tree or shrub comprising the steps of cleaning the wound site by removing sufficient wood to provide an elliptical or oval site wherein all damaged or diseased wood is removed, applying a coating mixture of fiberglass resin and hardener to said site, whereby air and moisture are excluded from said wound site by the resultant coating.

2. Method as in claim 1 wherein a fiberglass cloth is fastened to the wound site, completely covering the same prior to application of said mixture.

3. Method as in claim 2 wherein an additional mixture of fiberglass resin and hardener is applied to said wound site prior to covering the same with said fiberglass cloth.

4. Method as in claim 1 or 5 wherein said wound site is fumigated prior to the application of said mixture.

5. The method of repairing a wound on a tree or shrub comprising the steps of cleaning the wound site by removing sufficient wood to provide an elliptical or oval site wherein all damaged or diseased wood is removed, and said wound site is shaped to provide a cavity and said cavity is filled with a foam selected from the group consisting of polystyrene, polyurethane or vinyl chloride foam, covering said filled cavity with fiberglass cloth, and applying a coating mixture of fiberglass resin and hardener on to said fiberglass cloth and to an extent that the entire wound site is sealed from ambient air and moisture by the resultant fiberglass coating.

6. A method as in claim 1 or 5 wherein said coating is stained.

* * * * *